US 6,536,742 B2

(12) United States Patent
Lotz et al.

(10) Patent No.: US 6,536,742 B2
(45) Date of Patent: Mar. 25, 2003

(54) MULTI-WAY COCK

(75) Inventors: Norbert Lotz, Escholzmatt (CH); Gunther Siegmeier, Escholzmatt (CH); Boris Hayoz, Selzach (CH); Alois Schlarb, Wolhusen (CH)

(73) Assignee: B. Braun Melsungen AG (DE)

( * ) Notice: Subject to any disclaimer, the term of this patent is extended or adjusted under 35 U.S.C. 154(b) by 0 days.

(21) Appl. No.: 09/819,878

(22) Filed: Mar. 28, 2001

(65) Prior Publication Data
US 2001/0025942 A1 Oct. 4, 2001

(30) Foreign Application Priority Data
Mar. 28, 2000 (DE) .................. 200 05 691 U

(51) Int. Cl.$^7$ ................................ F16K 5/04
(52) U.S. Cl. ........................ 251/297; 251/312
(58) Field of Search .................. 251/297, 309, 251/312; 137/625.47

(56) References Cited

U.S. PATENT DOCUMENTS

| 292,824 | A | * | 2/1884 | Kennedy | 251/311 |
|---|---|---|---|---|---|
| 1,299,428 | A | * | 4/1919 | Cheeks | 251/309 |
| 3,783,900 | A | | 1/1974 | Waldbillig | |
| 3,957,082 | A | | 5/1976 | Fuson et al. | |
| 4,147,184 | A | * | 4/1979 | Jess | 251/312 |
| 4,549,569 | A | * | 10/1985 | Taylor | 251/297 |
| 4,794,944 | A | * | 1/1989 | Henry | 251/312 |
| 4,809,949 | A | * | 3/1989 | Rakieski | 251/312 |
| 4,890,817 | A | | 1/1990 | Uri | |
| 5,183,077 | A | * | 2/1993 | Keiper | 251/297 |
| 5,832,959 | A | * | 11/1998 | Szymczakowski et al. | 137/625.47 |

FOREIGN PATENT DOCUMENTS

| DE | 17 50 867 | 5/1971 |
|---|---|---|
| DE | 25 14 613 | 10/1975 |
| DE | 30 19 426 A1 | 11/1981 |
| DE | 42 00 452 C2 | 7/1993 |
| DE | 44 04 865 C2 | 8/1995 |
| DE | 197 08 884 C2 | 9/1998 |
| DE | 197 28 234 A1 | 3/1999 |
| EP | 0 366 667 B1 | 4/1993 |
| EP | 0 733 836 A1 | 9/1996 |
| EP | 0 768 099 A1 | 4/1997 |

* cited by examiner

Primary Examiner—Henry C. Yuen
Assistant Examiner—John Bastianelli
(74) Attorney, Agent, or Firm—Schnader Harrison Segal & Lewis LLP

(57) ABSTRACT

A multi-way cock including a substantially hollow-cylindrical housing with attachment bores on its outer circumference; a plug rotatably mounted in the housing and having a through-channel transverse to an axis of rotation and which may be aligned with the attachment bores in the housing; axially protruding engagement elements having locking grooves arranged on a base portion of the housing, which housing is closed at its bottom; and locking projections on an inner circumference of the hollow-cylindrical plug which are sized and shaped to engage the locking grooves.

15 Claims, 5 Drawing Sheets

MULTI-WAY COCK

FIELD OF THE INVENTION

The invention relates to a multi-way cock, in particular, a three-way cock for medical devices carrying infusion solutions, liquid medicaments and the like.

BACKGROUND

In a multi-way cock, the cock plug can assume intermediate positions in which a line is not fully closed off or a connection is not fully open.

It would accordingly be advantageous to provide a multi-way cock in such a way that the opening and closing positions of the cock plug can be set precisely and the cock plug cannot readily be turned out from a set operating position.

SUMMARY OF THE INVENTION

The invention provides this advantage by virtue of the fact that locking arrangements acting in the radial direction are provided between plug and housing, by means of which locking arrangements the respective operating position of the plug is clearly pre-defined for operating personnel and the respective set operating position is also fixed.

BRIEF DESCRIPTION OF THE DRAWINGS

The invention is explained in more detail and by way of example with reference to the drawings, in which.

DETAILED DESCRIPTION

Figure 1:
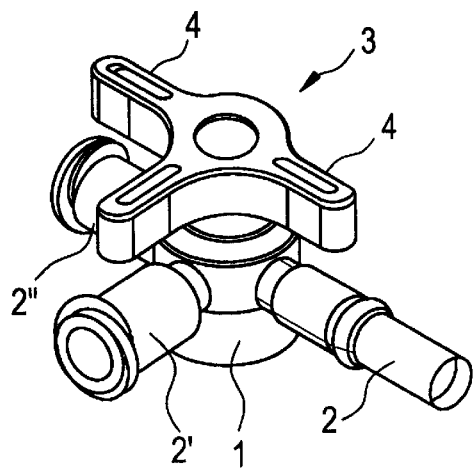
FIG. 1 shows a perspective view of a three-way cock.

The following description is intended to refer to specific embodiments of the invention illustrated in the drawings and is not intended to define or limit the invention, other than in the appended claims. Also, the drawings are not to scale and various dimensions and proportions are contemplated.

FIG. 1 shows a three-way cock with a hollow-cylindrical housing 1, with line attachments 2, 2' and 2" projecting radially from its circumference, the line attachments 2' and 2" each being provided with a Luer cone for attachment of a line. Reference number 3 designates a cock plug which can be turned in the housing 1 and which has three grip vanes 4 offset at 90°. Housing and plug are preferably made of plastic.

Figure 2:
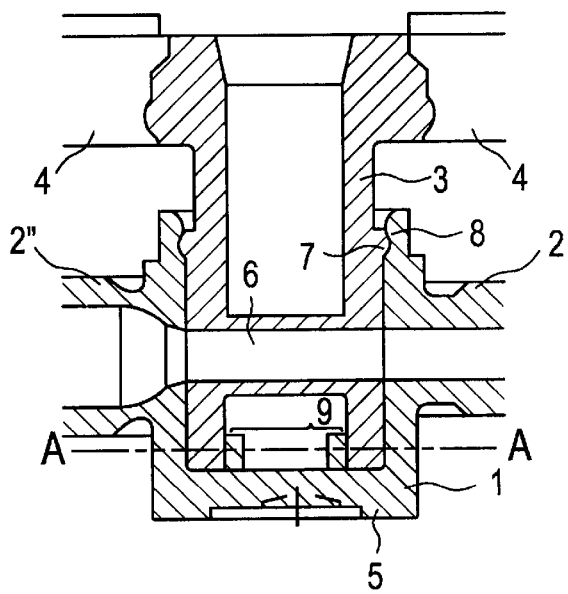
FIG. 2 shows a longitudinal section through a first embodiment.

FIG. 2 shows a longitudinal section of an embodiment in which the hollow-cylindrical housing 1 has a closed base 5 on which the end face of the hollow-cylindrical plug 3 bears, the latter having a through-channel 6 passing through it transverse to the axis of rotation, which through-channel 6 can be aligned with housing bores corresponding to the line attachments 2 to 2". In the upper area, the plug 3 has a bead 7 on the outer circumference, which bead 7 engages in an annular groove 8 on the inner circumference of the housing 1 and holds the plug 3 in the housing 1 in the axial direction. Around the through-channel 6, the plug 3 lies with its outer circumference bearing sealingly on the inner circumference of the housing 1.

Figure 3:
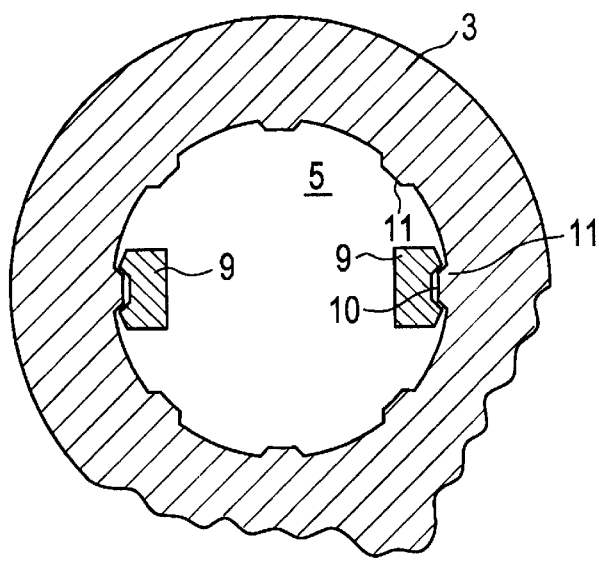
FIG. 3 shows a diagrammatic transverse section along the line A—A in FIG. 2.

Two axially projecting studs 9 are formed integrally at diametrically opposite points on the inside of the housing base 5, and these studs 9 are provided on their radially outer sides with axially extending flat grooves 10, as shown in FIG. 3, into which ribs or cams 11 arranged on the inner circumference of the plug 3 at the lower edge section can engage.

A plurality of axially projecting studs 9 can also be arranged on the housing base 5, and it is likewise possible to provide on the stud 9 a projecting rib 11 engaging in a corresponding recess or groove 10 on the inner circumference of the plug.

Ribs or cams 11 or corresponding grooves 10 are preferably provided on the circumference of the plug 3 at an angle spacing of about 45°.

By means of the ribs 11 projecting in the radial direction and the studs 9 which are elastic in the radial direction, the seal between plug and housing and the fit of the plug 3 in the housing 1 by means of the bead 7 are not impaired by the locking arrangement when the plug is turned.

Figure 4:
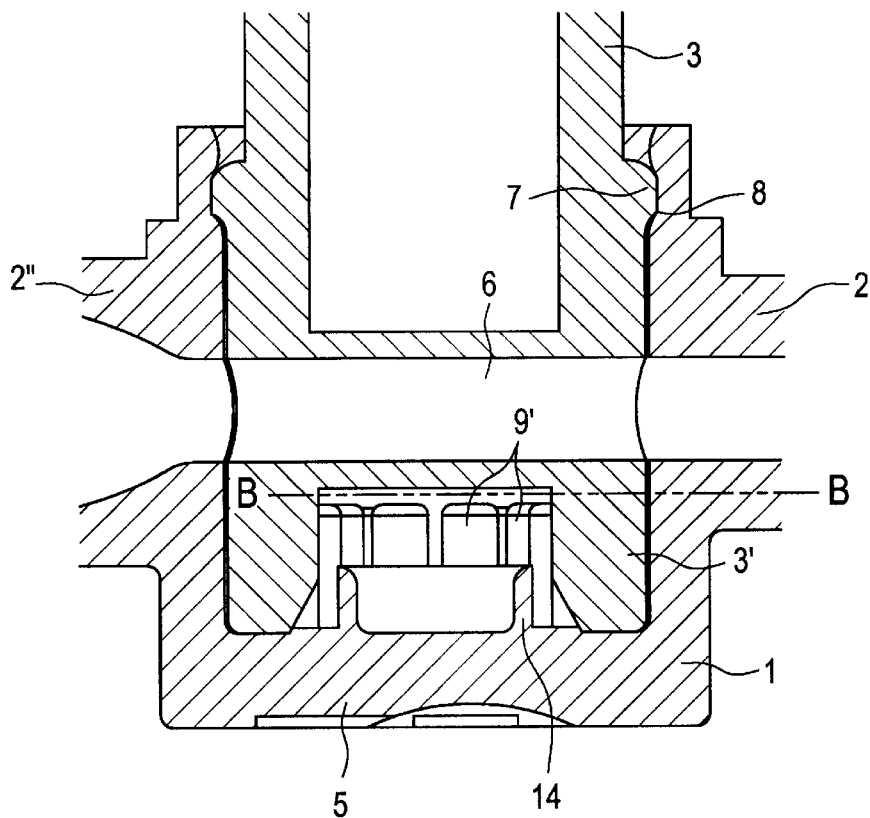
FIG. 4 shows a longitudinal section through a further embodiment.
Figure 5:
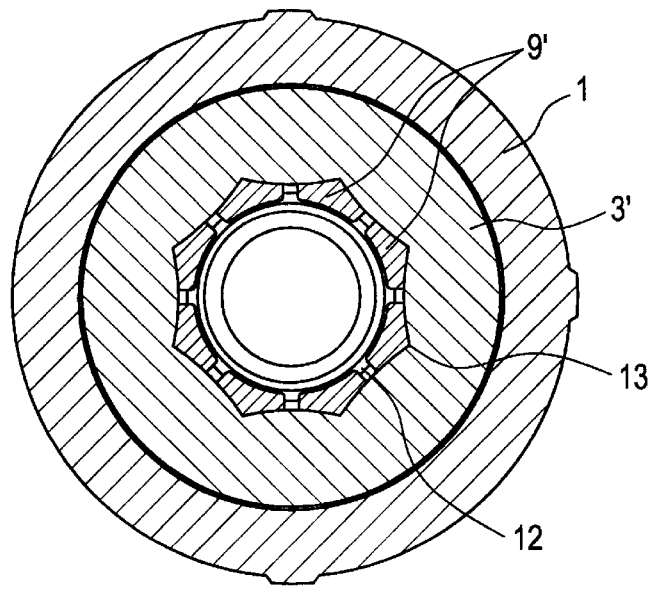
FIG. 5 shows a transverse section along the line B—B in FIG. 4.

FIGS. 4 and 5 show an embodiment in which a total of eight annularly arranged studs 9' are formed integrally on the housing base 5 in such a way that they are at a slight distance 12 from each other and are elastically movable in the radial direction. On their radially outward side, the individual studs 9' have a locking rib 13 with flat side flanks which adjoin the side flanks of the adjacent stud.

As the longitudinal section in FIG. 4 shows, an annular body 14 is formed integrally on the housing base 5 on the inner circumference of the studs 9', which annular body 14 extends to about half the height of the studs 9' and supports these in the radial direction.

The lower section 3' of the plug 3 has, on the inner circumference, a shape complementing the shape of the studs 9'. The inner circumference of the plug section 3' is of roughly octagonal design, in which the eight side faces are curved slightly radially inwards and the transitions between the side faces are rounded, corresponding to the shape of the locking ribs 13 on the outsides of the studs 9' and their slightly curved side flanks.

In the embodiment according to FIGS. 4 and 5, the radially inwardly curved side faces on the plug 3 can also be described as projections, and the corresponding depression between adjacent locking ribs 13 as a groove.

When the plug 3 is turned, a pressure is exerted on the sealing surface between plug and housing, so that the seal is not impaired.

Figure 6:
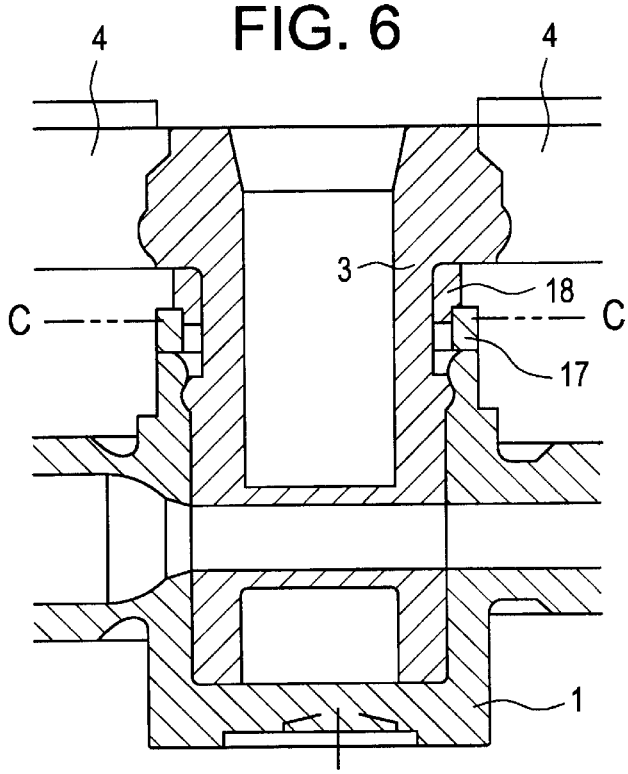
FIG. 6 shows a longitudinal section through another embodiment.
Figure 7:
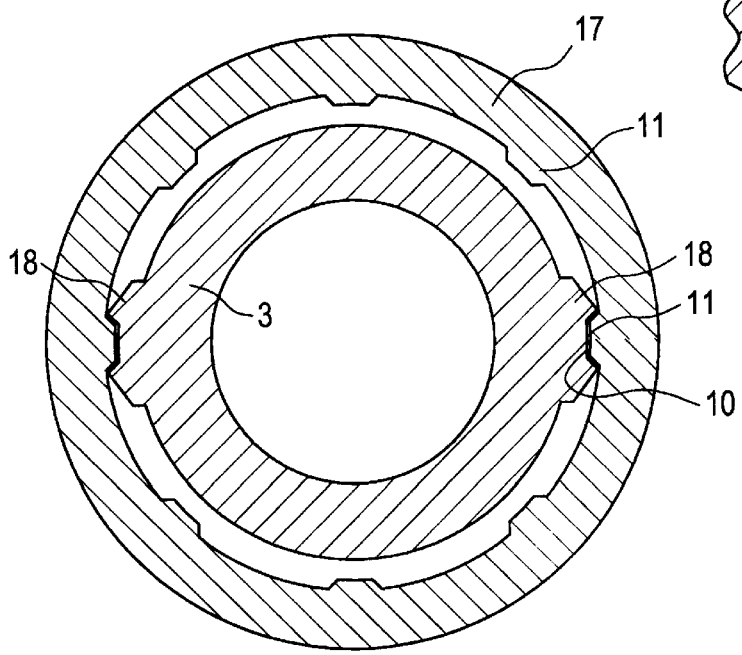
FIG. 7 shows a diagrammatic transverse section along the line C—C in FIG. 6.

FIGS. 6 and 7 show a further embodiment in which an annular body 17 is formed integrally on the upper edge of the housing 1 and has, on its inner circumference, cams or ribs 11 which are arranged at an angle spacing of about 45° and engage with grooves 10 on diametrically opposite projections 18, which are formed integrally on the plug 3 in the transition area between plug body and radially projecting grip vanes 4.

In accordance with the configuration in FIGS. 2 and 3, the annular body 17 can be divided into individual segments, each segment being provided with a cam or rib 11.

Figure 6A:
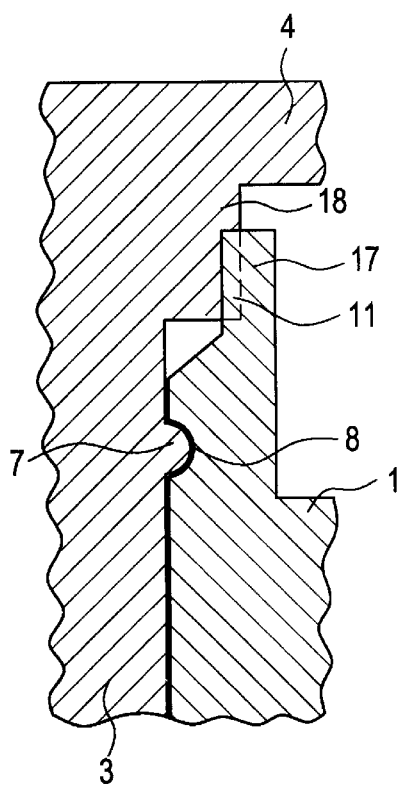
FIG. 6a shows an enlarged representation of the engagement area in FIG. 6, in section.

As the diagrammatic sectional view in FIG. 6a shows, the annular body 17 provided with the cams 11 has a smaller wall thickness than the adjoining wall section of the housing 1. In this way it is possible to ensure that, when the plug is turned, the hold on the bead 7 is not impaired.

Figure 8:
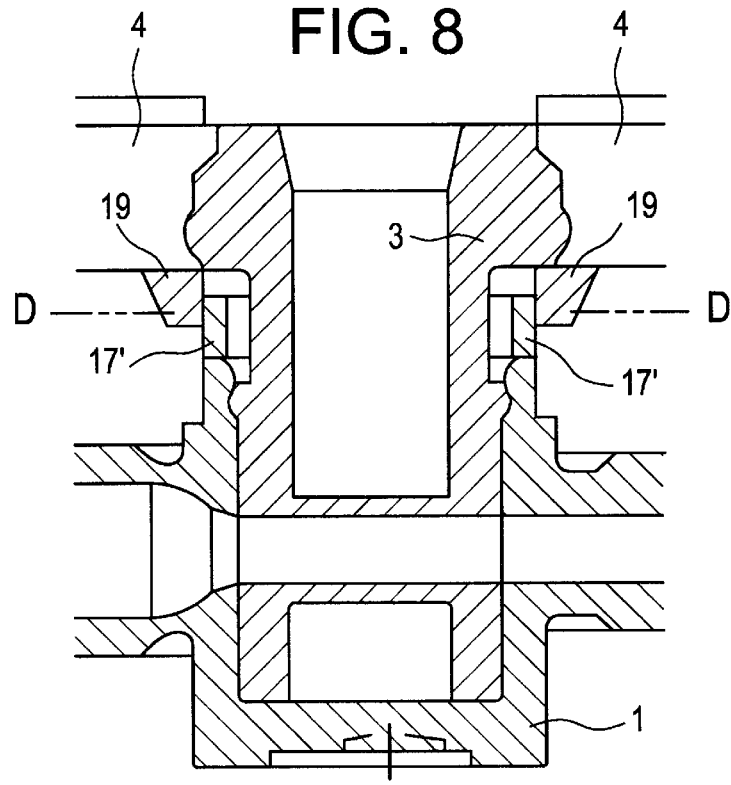
FIG. 8 shows a longitudinal section through a further embodiment.
Figure 9:
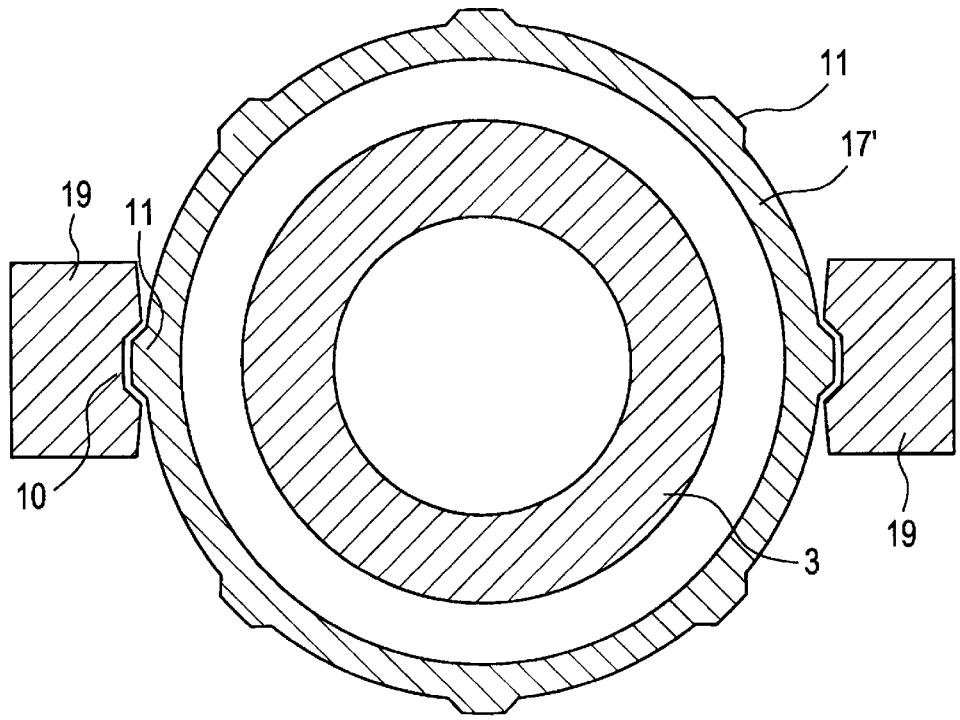
FIG. 9 shows a transverse section along the line D—D in FIG. 8.

In the embodiment according to FIGS. 8 and 9, cams or ribs 11 are arranged on the outer circumference of the annular body 17' formed integrally on the upper edge of the housing 1, which cams or ribs 11 lock in grooves 10 on two diametrically opposite projections 19 which are formed integrally on the underside of the grip vanes 4 of the plug 3. In this embodiment, radially inwardly directed forces act on the annular body 17' when the plug is turned, with the result that the hold of the plug on the bead 7 in the housing is not impaired.

In this embodiment according to FIGS. 8 and 9, the annular body 17' corresponding to the upper edge 17' of the housing 1 can have a greater diameter than the housing, in which case the projections 19 on the grip vanes 4 can be formed further out in the radial direction. By this means, a greater torque is applied to the locking arrangements when the cock plug is turned, as a result of which the adjustment of the plug is made easier.

A corresponding projection 19 for locking engagement with one of the cams 11 can also be formed on the third grip vane 4.

The embodiments according to FIGS. 6 to 9 are suitable for a multi-way cock without housing base 5, in other words, with a housing 1 open at the bottom.

Figure 10A:
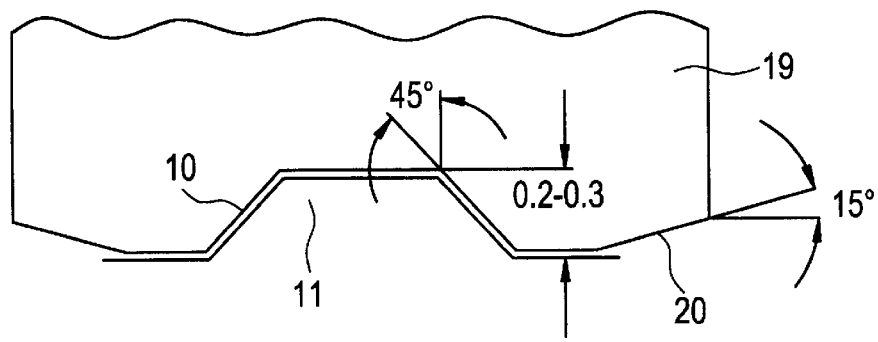
FIG. 10 shows an embodiment of ribs/cams and locking grooves.

FIG. 10 shows different rib and cam shapes, FIG. 10a representing in detail the cam shape used in the embodiments described above. The projection 19 in which the groove 10 is arranged has a beveled stop face 20 which lies at an angle of about 15° to the horizontal in FIG. 10a, while the side flanks of the rib or cam 11 and, correspondingly, the side faces of the groove 10 form an angle of about 45°.

Figure 10B:
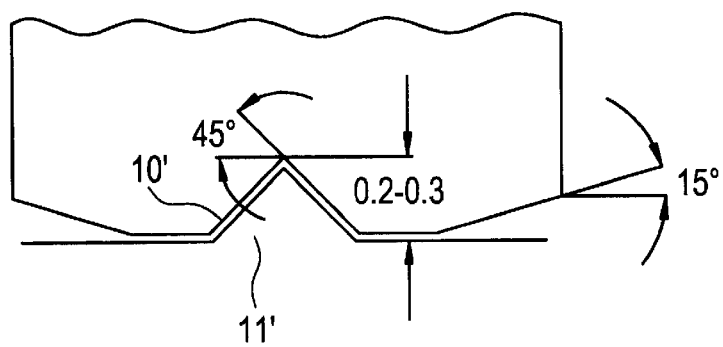

FIG. 10b shows a rib 11' which is substantially triangular in cross section, extends in the axial direction and engages in a groove 10' of complementary shape. In this embodiment, the height of the rib 11' or depth of the groove 10' is about 0.2 to 0.3 mm, as in the embodiment in FIG. 10a, and the side flanks of the rib 11' have an inclination of about 45°.

Figure 10C:
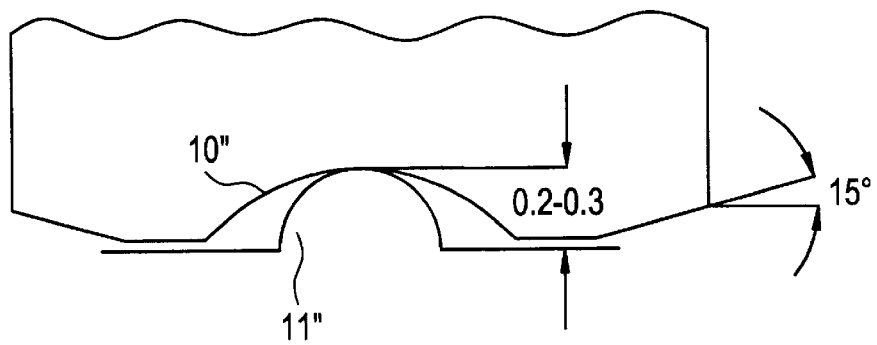

FIG. 10c shows a rib 11" of approximately semicircular cross section which engages in a concave groove 10" whose curvature is designed with a greater radius than the rounding of the rib 11".

Instead of the beveled surfaces represented in FIGS. 10a and 10b, rounded surface sections can also be provided to make the locking process smoother.

Various modifications of the described structural configurations are possible. Thus, for example, instead of a closed base 5 of the housing 1, webs arranged in a star shape can be provided extending radially inwards from the circumference of the housing 1, and the studs 9 provided for locking engagement can be formed integrally on these webs.

In the embodiment according to FIGS. 2 and 3, it is also possible, for example, to provide a bore in the middle of the base 5 between the studs 9, so that the base of the housing is open. The studs 9 are in this case formed integrally on an annular area about the bore. Such a bore can be provided also in the embodiments of FIGS. 4, 6 and 8.

According to a further embodiment, in the structure according to FIGS. 8 and 9 it is possible to provide, instead of the projection 19, an annular body (not shown) which is formed integrally on the underside of the grip vanes 4 or otherwise secured and which engages over the annular body 17' formed integrally on the housing, as is shown in the sectional representation in FIG. 8. In such an embodiment, the annular body arranged on the grip vanes 4 surrounds the annular body 17' in the cross sectional view according to FIG. 9, and, during a locking procedure or relative turning between the two annular bodies, forces distributed about the circumference act radially inwardly on the housing. In the embodiment according to FIG. 9, upon relative turning between projections 19 and annular body 17', radially inwardly directed forces act only on diametrically opposite locations.

What is claimed is:

1. A multi-way cock comprising:
    a substantially hollow-cylindrical housing having attachment bores on an outer circumference thereof; and
    a plug rotatably mounted in the housing and having a through-channel transverse to an axis of rotation and which may be aligned with the attachment bores in the housing, the plug having a hollow-cylindrical base portion;
    wherein axially protruding engagement elements are arranged on a radially extending base portion of the hollow cylindrical housing such that the engagement elements protrude into the hollow-cylindrical base portion of the plug, and wherein the engagement elements have locking grooves on a radial outer side for engagement with locking projections provided on an inner circumference of the hollow-cylindrical base portion of the plug.

2. The multi-way cock according to claim 1, wherein the engagement elements are diametrically opposite studs.

3. The multi-way cock according to claim 1, wherein the engagement elements are studs arranged in an annular configuration.

4. The multi-way cock according to claim 3, wherein the engagement elements are elastically movable in the radial direction and are supported by an annular body formed integrally inside the annularly arranged engagement elements on the base portion of the housing, wherein the annular body has a radial distance from engagement elements for allowing elastic movement of the engagement elements in the radial direction.

5. A multi-way cock according to claim 1, wherein the housing is provided with a closed base portion.

6. The multi-way cock according to claim 1, in which locking positions are arranged at an angle space of about 45°.

7. A multi-way cock comprising:
    a substantially hollow-cylindrical housing having attachment bores on an outer circumference thereof; and
    a plug rotatably mounted in the housing and having a through-channel transverse to an axis of rotation and which may be aligned with the attachment bores in the housing, the plug having a hollow-cylindrical base portion;

wherein axially protruding engagement elements are arranged on a radially extending base portion of the hollow-cylindrical housing such that the engagement elements protrude into the hollow-cylindrical base portion of the plug, and wherein the engagement elements have rib-shaped locking projections extending radially outwardly for engagement with locking grooves provided on an inner circumference of the hollow-cylindrical base portion of the plug.

8. The multi-way cock according to claim 7, wherein the inner circumference of the hollow-cylindrical base portion of the plug is a substantially octagonal shape, individual side faces of the inner circumference being curved inwards, and wherein the rib-shaped locking projections of the engagement elements engage into the locking groove formed by adjacent curved side faces on the inner circumference of the hollow-cylindrical base portion of the plug.

9. The multi-way cock according to claim 8, wherein the engagement elements are elastically movable in the radial direction and are supported by an annular body formed integrally inside the annularly arranged engagement elements.

10. The multi-way cock according to claim 7, wherein the engagement elements are diametrically opposite studs.

11. The multi-way cock according to claim 7, wherein the engagement elements are studs arranged in an annular configuration.

12. The multi-way cock according to claim 11, wherein the engagement elements are elastically movable in the radial direction and are supported by an annular body formed integrally inside the annularly arranged engagement elements on the base portion of the housing, wherein the annular body has a radial distance from the engagement elements to allow elastic movement of the engagement elements in the radial direction.

13. A multi-way cock according to claim 7, wherein the housing is provided with a closed base portion.

14. The multi-way cock according to claim 7, wherein the locking projections are arranged on diametrically opposite locations of the plug.

15. The multi-way cock according to claim 7, in which locking positions are arranged at an angle space of about 45°.

* * * * *